(12) United States Patent
Chin et al.

(10) Patent No.: US 9,746,443 B2
(45) Date of Patent: Aug. 29, 2017

(54) IN-SITU PATHOGEN DETECTION USING MAGNETOELASTIC SENSORS

(71) Applicants: Bryan A. Chin, Auburn, AL (US); Zhongyang Cheng, Auburn, AL (US); Suiqiong Li, Auburn, AL (US); Mi-Kyung Park, Auburn, AL (US); Shin Horikawa, Auburn, AL (US); Yating Chai, Auburn, AL (US); Kanchana Weerakoon, Auburn, AL (US); Stevie R. Best, Auburn, AL (US); Martin E. Baltazar-Lopez, Auburn, AL (US); Howard C. Wikle, Auburn, AL (US)

(72) Inventors: Bryan A. Chin, Auburn, AL (US); Zhongyang Cheng, Auburn, AL (US); Suiqiong Li, Auburn, AL (US); Mi-Kyung Park, Auburn, AL (US); Shin Horikawa, Auburn, AL (US); Yating Chai, Auburn, AL (US); Kanchana Weerakoon, Auburn, AL (US); Stevie R. Best, Auburn, AL (US); Martin E. Baltazar-Lopez, Auburn, AL (US); Howard C. Wikle, Auburn, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 276 days.

(21) Appl. No.: 14/064,308

(22) Filed: Oct. 28, 2013

(65) Prior Publication Data
US 2014/0120524 A1 May 1, 2014

Related U.S. Application Data

(60) Provisional application No. 61/718,911, filed on Oct. 26, 2012.

(51) Int. Cl.
  *G01N 27/72* (2006.01)
  *G01N 27/74* (2006.01)
  *G01N 33/543* (2006.01)

(52) U.S. Cl.
  CPC ........... *G01N 27/72* (2013.01); *G01N 27/745* (2013.01); *G01N 33/54373* (2013.01)

(58) Field of Classification Search
  CPC . G01N 27/72; G01N 33/54373; G01N 27/745
  See application file for complete search history.

(56) References Cited

U.S. PATENT DOCUMENTS

| 2,353,180 A | 7/1944 | Egon |
| 6,397,661 B1 | 6/2002 | Grimes et al. |

(Continued)

OTHER PUBLICATIONS

ISA/US, International Search Report and Written Opinion for PCT/US2013/066922, Mar. 18, 2014, 10 pages.

(Continued)

*Primary Examiner* — Melanie Y Brown
(74) *Attorney, Agent, or Firm* — Barnes & Thornburg LLP (57) ABSTRACT

In at least one illustrative embodiment, a method for in-situ pathogen detection may comprise distributing one or more magnetoelastic measurement sensors on a surface of a test object, wherein each of the one or more magnetoelastic measurement sensors includes a biorecognition element configured to bind with a pathogen to cause a shift in a characteristic frequency of the associated measurement sensor; applying a varying magnetic field, using a test coil, to the one or more magnetoelastic measurement sensors distributed on the surface of the test object, wherein the test object is positioned outside of an inner volume defined by the test coil; detecting a frequency response of the one or more magnetoelastic measurement sensors using the test coil, while applying the varying magnetic field; and deter- (Continued)

mining whether the pathogen is present based on the detected frequency response of the one or more magnetoelastic measurement sensors.

18 Claims, 4 Drawing Sheets

(56) References Cited

U.S. PATENT DOCUMENTS

| | | |
|---|---|---|
| 7,113,876 B2 | 9/2006 | Zeng et al. |
| 7,138,238 B2 | 11/2006 | Vodyanoy et al. |
| 7,267,993 B2 | 9/2007 | Pentrenko et al. |
| 7,473,550 B2 | 1/2009 | Vodyanoy et al. |
| 7,670,765 B2 | 3/2010 | Petrenko et al. |
| 7,759,134 B2 | 7/2010 | Chin et al. |
| 2002/0153882 A1* | 10/2002 | Grimes .................. G01N 27/72 324/209 |
| 2002/0166382 A1* | 11/2002 | Bachas .............. G01N 33/4905 73/579 |
| 2004/0113801 A1 | 6/2004 | Gustafson et al. |
| 2005/0074904 A1 | 4/2005 | Chin et al. |
| 2008/0071487 A1 | 3/2008 | Zeng et al. |
| 2008/0261261 A1* | 10/2008 | Grimes .............. G01N 33/4905 435/29 |
| 2009/0145239 A1 | 6/2009 | Girshovich et al. |
| 2009/0284249 A1 | 11/2009 | Syracuse et al. |
| 2009/0302498 A1* | 12/2009 | Nedestam ................ A61F 13/42 264/263 |
| 2010/0052669 A1* | 3/2010 | Kwun .................. G01N 29/043 324/240 |
| 2011/0298455 A1* | 12/2011 | Liang ................ B01L 3/502715 324/252 |
| 2012/0119732 A1* | 5/2012 | Rose .................. G01N 29/2412 324/240 |
| 2012/0280682 A1 | 11/2012 | Cheng et al. |

OTHER PUBLICATIONS

Zhang et al., "Development of Highly Sensitive Handheld Device for Real-Time Detection of Bacteria in Food," Proc. of SPIE vol. 7676, 2010, 12 pages.

Chai et al., "Design of a Surface-Scanning Coil Detector for Direct Bacteria Detection on Food Surfaces Using a Magnetoelastic Biosensor," J. Applied Physics, 2013, 8 pages, vol. 114,104504.

Chai et al., "A Surface-Scanning Coil Detector for Real-Time, In-Situ Detection of Bacteria on Fresh Food Surfaces," Biosensors and Bioelectronics, 2013, pp. 311-317, vol. 50.

Li et al., "Direct detection of *Salmonella typhimurium* on flesh produce using phage-based magnetoelastic biosensors", Biosensors and Bioelectronics, Elsevier BV, NL, vol. 26, No. 4, pp. 1313-1319, Dec. 15, 2010.

Extended European Search Report, European Application No. 13848916.6-1408 / 2912645 PCT/US2013/066922, dated Jun. 7, 2016, 11 pages.

C. Liang et al., "Correction for Longitudinal Mode Vibration in Thin Slender Beams," Applied Physics Letters, 2007, vol. 90, pp. 221912-1 to 221912-3.

C.A. Grimes et al., "Remote Query Pressure Measurement Using Magnetoelastic Sensors," Review of Scientific Instruments, 1999, vol. 70, pp. 4711-4714.

M.L. Johnson et al., "A Wireless Biosensor Using Microfabricated Phage-Interfaced Magnetoelastic Particles," Sensors and Actuators A-Physical, 2008, vol. 144, pp. 38-47.

* cited by examiner

IN-SITU PATHOGEN DETECTION USING MAGNETOELASTIC SENSORS

CROSS-REFERENCE TO RELATED APPLICATION

This application claims priority to U.S. Provisional Application Ser. No. 61/718,911, filed Oct. 26, 2012, the entire disclosure of which is hereby incorporated by reference.

STATEMENT REGARDING FEDERALLY SPONSORED RESEARCH

This invention was made with government support under Grants No. 2009-35603-05051, 2010-34605-20651, and 2011-51181-30642A, awarded by the U.S. Department of Agriculture, and Grant No. CBET-1157962, awarded by the National Science Foundation. The government has certain rights in the invention.

BACKGROUND

Foodborne illnesses are primarily caused by food contaminated with pathogenic microorganisms in the field or during food processing under insanitary conditions. Hence, surveillance of bacterial contamination of fresh produce through the food supply chain is of great importance to the food industry. However, such surveillance is a challenge since the food supply chain is a lengthy trail with many opportunities to cause food contamination. Food products may be cleaned at the harvesting site, transported to a warehouse, re-cleaned, and repackaged several times before reaching retail outlets.

Typical microbiological methods for pathogen detection, such as colony counting, immunoassay, and polymerase chain reaction (PCR), offer very high sensitivities. However, they require pre-analytical sample preparation, which generally includes sample collecting, separating target pathogen cells from food, increasing cell concentration, and achieving analysis volume from bulk samples before detection. These processes are time consuming, resulting in delays in obtaining the screening results. More importantly, food samples have to be delivered to laboratories for culture preparation and analysis. Label-free biosensors are available in today's market. However, they also require sample preparation prior to the actual testing (i.e. sampling from fresh produce, filtration and purification of the collected samples, and injection of the filtered/purified samples into a flow system where a biosensor resides). Due to the complexity of these test procedures and the requirements of expensive equipment and highly trained personnel, current food safety controls mainly rely on control of worker/environment hygiene in the food processing industry, rather than the direct pathogen detection.

Free-standing phage-based magnetoelastic biosensors have been investigated as a label-free wireless biosensor system for real-time pathogen detection. The magnetoelastic biosensor is typically composed of a magnetoelastic resonator that is coated with a bio-molecular recognition element that binds specifically with a target pathogen. Once the biosensor comes into contact with the target pathogen, binding occurs, causing an increase in the mass of the resonator resulting in a decrease in the resonant frequency of the sensor (as well as other characteristic frequencies of the sensor). However, typical exciter/detector coils do not detect magnetoelastic biosensors positioned outside of the coil's interior geometry.

When bacteria cells contaminate a food surface, the distribution of bacteria cells is typically highly non-uniform. The pathogen cells can migrate and move along the food surface and aggregate at regions containing nutrients and water needed to sustain life. By way of example, on a tomato spiked with a high concentration of *Salmonella*, cells may typically cover almost the whole drop area due to the high concentration of bacteria in the liquid. With a decrease in suspension concentration, the number of *Salmonella* cells on the surface may decrease and the distribution of cells over the surface may become more non-uniform. As the water of the spiking solution evaporates, the *Salmonella* cells typically aggregate to areas of residual moisture and form clusters. Therefore, the distribution of *Salmonella* cells may become highly non-uniform on the tomato surface as the concentration of *Salmonella* in the spiking solutions decreases. Additionally, variances in the roughness of the tomato, curvature of the tomato surface, punctures, defects, and wounds may contribute to a non-uniform distribution of *Salmonella* on the tomato surface.

SUMMARY

According to one aspect, a method for in-situ pathogen detection may comprise distributing one or more magnetoelastic measurement sensors on a surface of a test object, wherein each of the one or more magnetoelastic measurement sensors includes a biorecognition element configured to bind with a pathogen to cause a shift in a characteristic frequency of the associated measurement sensor; applying a varying magnetic field, using a test coil, to the one or more magnetoelastic measurement sensors distributed on the surface of the test object, wherein the test object is positioned outside of an inner volume defined by the test coil; detecting a frequency response of the one or more magnetoelastic measurement sensors using the test coil, while applying the varying magnetic field; and determining whether the pathogen is present based on the detected frequency response of the one or more magnetoelastic measurement sensors. Applying the varying magnetic field may cause vibration of the one or more magnetoelastic measurement sensors, and detecting the frequency response may comprise measuring, using the test coil, a magnetic field generated by the vibration of the one or more magnetoelastic measurement sensors.

In some embodiments, the test coil may be a focused-field flat coil. The biorecognition element may comprise a bacteriophage that is genetically engineered to bind with the pathogen.

In some embodiments, the method may further comprise applying a uniform magnetic field to the one or more magnetoelastic measurement sensors to align the one or more magnetoelastic measurement sensors prior to applying the varying magnetic field. The method may further comprise applying the uniform magnetic field to the one or more magnetoelastic measurement sensors to bias the one or more magnetoelastic measurement sensors while applying the varying magnetic field.

In some embodiments, applying the varying magnetic field may comprise varying a frequency of the varying magnetic field through a range including the characteristic frequency of each of the one or more magnetoelastic measurement sensors when the biorecognition element has not bound with the pathogen. The range may include one or more values that are one half of the characteristic frequency of each of the one or more magnetoelastic measurement sensors when the biorecognition element has not bound with the pathogen. Detecting the frequency response may comprise measuring an impedance of the test coil while varying the frequency of the varying magnetic field through the range.

In some embodiments, the method may further comprise distributing one or more magnetoelastic control sensors on the surface of the test object, wherein each of the one or more magnetoelastic control sensors does not include the biorecognition element; applying the varying magnetic field, using the test coil, to the one or more magnetoelastic control sensors distributed on the surface of the test object; and detecting a frequency response of the one or more magnetoelastic control sensors using the test coil, while applying the varying magnetic field. Determining whether the pathogen is present may comprise determining whether the pathogen is present based on both the detected frequency response of the one or more magnetoelastic measurement sensors and the detected frequency response of the one or more magnetoelastic control sensors.

In some embodiments, detecting the frequency response of the one or more magnetoelastic measurement sensors may comprise measuring a shifted characteristic frequency of the one or more magnetoelastic measurement sensors caused by the biorecognition element binding with the pathogen. Detecting the frequency response of the one or more magnetoelastic control sensors may comprise measuring a control characteristic frequency of the one or more magnetoelastic control sensors. Determining whether the pathogen is present may comprise comparing the shifted characteristic frequency and the control characteristic frequency. Comparing the shifted characteristic frequency and the control characteristic frequency may comprise determining whether the shifted characteristic frequency is statistically significantly less than the control characteristic frequency.

In some embodiments, the method may further comprise distributing one or more additional magnetoelastic measurement sensors on the surface of the test object, wherein each of the one or more additional measurement sensors includes a different biorecognition element configured to bind with a different pathogen to cause a shift in a characteristic frequency of the associated additional measurement sensor; applying the varying magnetic field, using the test coil, to the one or more additional magnetoelastic measurement sensors distributed on the surface of the test object; detecting a frequency response of the one or more additional magnetoelastic measurement sensors using the test coil, while applying the varying magnetic field; and determining whether the different pathogen is present based on the detected frequency response of the one or more additional magnetoelastic measurement sensors.

In some embodiments, the test object may be a food item or a food preparation apparatus. The method may further comprise using a magnet to remove the one or more magnetoelastic measurement sensors from the test object, after determining whether the pathogen is present.

According to another aspect, an in-situ pathogen detection system may comprise one or more magnetoelastic measurement sensors each including a biorecognition element configured to bind with a pathogen to cause a shift in a characteristic frequency of the associated measurement sensor; a test coil configured to (i) apply a varying magnetic field to the one or more magnetoelastic measurement sensors and (ii) detect a frequency response of the one or more magnetoelastic measurement sensors to the applied varying magnetic field, while the one or more magnetoelastic measurement sensors are positioned on a surface of a test object that is outside of an inner volume defined by the test coil; and a controller coupled to the test coil and configured to (i) transmit a first signal that causes the test coil to generate the varying magnetic field, (ii) receive a second signal indicative of the frequency response of the one or more magnetoelastic measurement sensors detected by the test coil, and (iii) determine whether the pathogen is present based on the second signal. The test coil may be configured to detect the frequency response by measuring a magnetic field generated by vibration of the one or more magnetoelastic measurement sensors in response to the applied varying magnetic field.

In some embodiments, the test coil may comprise a number of loops surrounding the inner volume and a glass core positioned within the inner volume. The test coil may be a focused-field flat coil. The test coil may comprise a pair of partially overlapping flat coils having opposite winding directions. The test coil may further comprise a backing formed of a high magnetic permeability material. The biorecognition element comprises a bacteriophage that is genetically engineered to bind with the pathogen.

In some embodiments, the in-situ pathogen detection system may further comprise a magnetic field generator configured to apply a uniform magnetic field to align the one or more magnetoelastic measurement sensors prior to application of the varying magnetic field. The magnetic field generator may be further configured to apply the uniform magnetic field to bias the one or more magnetoelastic measurement sensors during application of the varying magnetic field.

In some embodiments, the first signal may cause a frequency of the varying magnetic field generated by the test coil to vary through a range including the characteristic frequency of each of the one or more magnetoelastic measurement sensors when the biorecognition element has not bound with the pathogen. The range may include one or more values that are one half of the characteristic frequency of each of the one or more magnetoelastic measurement sensors when the biorecognition element has not bound with the pathogen. The second signal may be indicative of an impedance of the test coil while varying the frequency of the varying magnetic field through the range.

In some embodiments, the in-situ pathogen detection system may further comprise one or more magnetoelastic control sensors that do not include the biorecognition element. The test coil may be further configured to (i) apply the varying magnetic field to the one or more magnetoelastic control sensors and (ii) detect a frequency response of the one or more magnetoelastic control sensors to the applied varying magnetic field, while the one or more magnetoelastic control sensors are positioned on the surface of the test object. The second signal may also be indicative of the frequency response of the one or more magnetoelastic control sensors detected by the test coil.

In some embodiments, the second signal may be indicative of (i) a shifted characteristic frequency of the one or more magnetoelastic measurement sensors caused by binding of the biorecognition element with the pathogen and (ii) a control characteristic frequency of the one or more magnetoelastic control sensors. The controller may be configured to determine whether the pathogen is present by determining whether the shifted characteristic frequency is statistically significantly less than the control characteristic frequency.

In some embodiments, the in-situ pathogen detection system may further comprise one or more additional magnetoelastic measurement sensors each including a different biorecognition element configured to bind with a different pathogen to cause a shift in a characteristic frequency of the associated additional measurement sensor. The test coil may be further configured to (i) apply the varying magnetic field to the one or more additional magnetoelastic measurement sensors and (ii) detect a frequency response of the one or more additional magnetoelastic measurement sensors to the applied varying magnetic field, while the one or more additional magnetoelastic measurement sensors are positioned on the surface of the test object. The second signal may also be indicative of the frequency response of the one or more additional magnetoelastic measurement sensors detected by the test coil, and the controller may be further configured to determine whether the different pathogen is present based on the second signal.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the present disclosure.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 1:
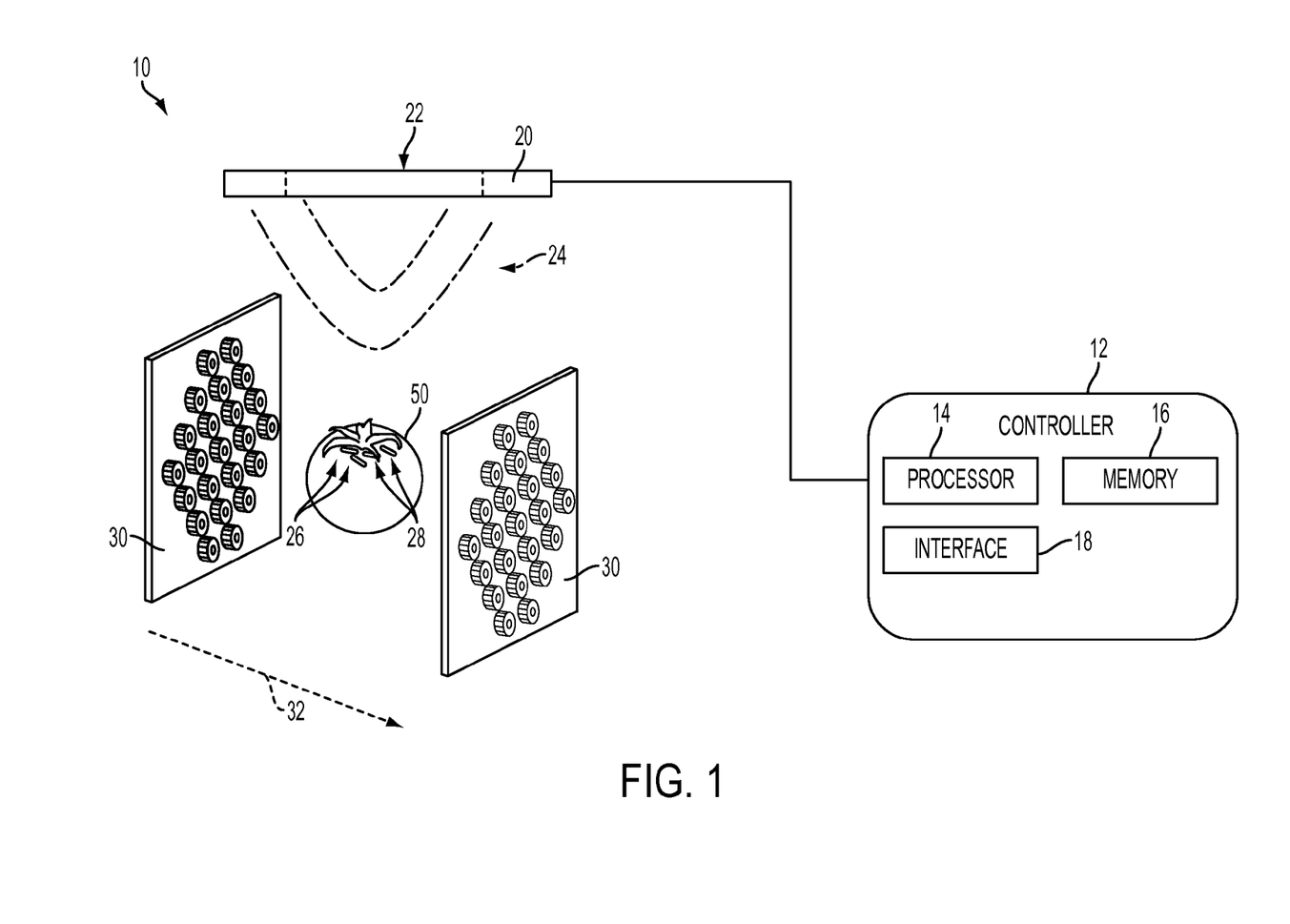
FIG. 1 is a simplified schematic diagram of an in-situ pathogen detection using magnetoelastic sensors.

Referring now to FIG. 1, a simplified schematic diagram of one illustrative embodiment of an in-situ pathogen detection system 10 is shown. The system 10 includes a controller 12 coupled to a test coil 20. The controller 12 causes the test coil 20 to apply a varying magnetic field 24 to a number of magnetoelastic measurement sensors 26. In some embodiments, the test coil 20 may also apply the varying magnetic field 24 to a number of magnetoelastic control sensors 28. The sensors 26, 28 are distributed upon a surface of a test object 50, which is illustratively embodied in FIG. 1 as a tomato. The test object 50 may be embodied as any object upon which pathogens may be detected including a food item (e.g., a fresh fruit or vegetable) or a food preparation apparatus (e.g., a cooking utensil or food preparation counter). The controller 12 measures a magnetic field produced by the sensors 26, 28 in response to the varying magnetic field 24 and determines a characteristic frequency of the sensors 26, 28. This characteristic frequency is related to the resonant frequency of the sensors 26, 28, as well as other material properties (e.g., the magnetoelastic coupling coefficient) and the environment (e.g., friction forces or damping effects). As described further below, pathogens present on the surface of the test object 50 may bind with the measurement sensors 26, causing an increase in the mass of the measurement sensors 26 and a corresponding decrease in the characteristic frequency. The system 10 determines whether the pathogen is present by determining whether the characteristic frequency shifts. The system 10 may thus detect the pathogen in real time. Multiple pathogens may be detected simultaneously by using separate groups of measurement sensors 26 and/or control sensors 28, with each group of measurement sensors 26 binding to a different target pathogen.

Accordingly, the system 10 may provide a wireless, inexpensive, accurate, portable, and easy-to-use method for real-time, remote, and specific detection of foodborne pathogens. As one exemplary use, the disclosed technologies are able to directly detect *Salmonella Typhimurium* in food products without the requirement of pre-analysis culture preparation. The in-situ detection method may be performed on fresh food surfaces, such as food produce surfaces or meat surfaces, or on food processing facility surfaces, such as a food processing line surface or a kitchen table surface. The disclosed system and method do not require a sample preparation process and may be adapted for application at different critical control points along the food supply chain, such as in agriculture fields, storage houses, or grocery stores.

As described briefly above, the system 10 includes the controller 12. The controller 12 is responsible for activating or energizing electronically-controlled components of the system 10, including the test coil 20. The controller 12 is also responsible for interpreting electrical signals received from other components of the system 10, including the test coil 20. To do so, the controller 12 may include a number of electronic components commonly associated with units utilized in the control of electronic and electromechanical systems. For example, the controller 12 may include, amongst other components customarily included in such devices, a processor 14 and a memory device 16. The processor 14 may be any type of device capable of executing software or firmware, such as a microcontroller, microprocessor, digital signal processor, or the like. The memory device 16 may be embodied as one or more non-transitory, machine-readable media. The memory device 16 is provided to store, amongst other things, instructions in the form of, for example, a software routine (or routines) which, when executed by the processor 14, allows the controller 12 to perform in-situ pathogen detection using the other components of the system 10.

The controller 12 also includes an analog interface circuit 18. The analog interface circuit 18 converts output signals (e.g., from the test coil 20) into signals which are suitable for presentation to an input of the processor 14. In particular, the analog interface circuit 18, by use of a network analyzer, an analog-to-digital (A/D) converter, or the like, converts analog signals into digital signals for use by the processor 14. Similarly, the analog interface circuit 18 converts signals from the processor 14 into output signals which are suitable for presentation to the electrically-controlled components associated with system 10 (e.g., the test coil 20). In particular, the analog interface circuit 18, by use of a variable-frequency signal generator, digital-to-analog (D/A) converter, or the like, converts digital signals generated by the processor 14 into analog signals for use by the electronically-controlled components associated with the system 10. It is contemplated that, in some embodiments, the analog interface circuit 18 (or portions thereof) may be integrated into the processor 14.

As also mentioned above, the system 10 includes the test coil 20. The test coil 20 generally includes a number of loops of conducting material that define an inner volume 22 of the test coil 20. In some embodiments, the test coil 20 may have a solid material (e.g., glass) positioned within the inner volume 22. In the illustrative embodiment of the system 10, the test coil 20 is used both as an energizing excitation source for the sensors 26, 28 and as a remote, non-contacting detector of signals received from the magnetoelastic sensors 26, 28. As such, the test coil 20 is configured to generate the varying magnetic field 24 outside of its inner volume 22. That is, the test coil 20 generates a varying magnetic field 24 that has sufficient strength outside of the inner volume 22 to interact with the magnetoelastic sensors 26, 28 as described below. Of course, the test coil 20 may also generate a magnetic field within the inner volume 22. In some embodiments, the test coil 20 may be a solenoid with loops having a generally rectangular cross-section. For example, the test coil 20 may be embodied as a focused-field flat coil. One embodiment of such a focused-field flat coil is further described below, in connection with FIGS. 3 and 4. To improve performance of the system 10, the test coil 20 may be impedance-matched to the electrical circuitry of the controller 12. For example, an output of the controller 12 may have a characteristic output impedance of about 50Ω, and the test coil 20 may be designed to have an impedance of about 50Ω.

In some illustrative embodiments the test coil 20 may be a flat coil that is fabricated directly on a printed circuit board (PCB). The test coil 20 may be fabricated with geometric shapes and conductor lengths appropriate for the inductance required at the electrical signal frequencies applied. Fabrication on PCBs often employs methods of microfabrication where photolithography techniques are used to produce detailed patterns. For the size of measurement sensors 26 described herein (i.e., millimeter and sub-millimeter), excitation and resonance frequencies may be in the medium frequency range (MF: 300 kHz-3 MHz) and/or the high frequency range (HF: 3 MHz-30 MHz). PCB-based inductor designs at MF and HF ranges may be multi-layer stacked and/or generally spiral in various geometrical patterns. These geometric patterns may be circular, ellipsoidal, or polygonal (such as square, rectangular, hexagonal, octagonal, etc.) spirals.

The measurement sensors 26 are small devices made of a magnetoelastic material coated with a biorecognition element 36 that binds to a particular pathogen. For example, the biorecognition element 36 may include antibodies or genetically engineered phages that bind to particular bacteria, such as *Salmonella Typhimurium*. The magnetoelastic material converts magnetic energy to mechanical energy and vice versa. In other words, magnetoelastic materials generate mechanical strain when the magnetic energy is applied and generate magnetic energy in response to mechanical strain. In the illustrative embodiment, the measurement sensors 26 are embodied as thin strips of material that are actuated into resonance by application of the varying magnetic field 24. Upon contact with the specific target pathogen, the pathogen binds with the biorecognition element 36 and increases the mass of the measurement sensor 26. This additional mass causes the characteristic frequency of the measurement sensors 26 to decrease. The characteristic frequency may be measured by the test coil 20, allowing quantitative detection and characterization of the pathogen. In use, as described below, the measurement sensors 26 may be distributed on a surface of the test object 50 that is outside of the inner volume 22 of the test coil 20. One embodiment of a measurement sensor 26 is further described below in connection with FIG. 2.

The control sensors 28 are constructed similarly to the measurement sensors 26, except the control sensors 28 lack the biorecognition element 36. Similar to the measurement sensors 26, the control sensors 28 are made of the same magnetoelastic material and thus resonate when the varying magnetic field 24 is applied. However, the control sensors 28 do not bind with the target pathogen because they lack the biorecognition element 36. Thus, the characteristic frequency of the control sensors 28 does not change in response to the presence of the pathogen. In some embodiments, the characteristic frequency of the control sensors 28 may be slightly different than that of the measurement sensors 26 when no pathogen has been bound to the measurement sensors 26, allowing the sensors 26, 28 to be distinguished from one another.

As illustrated in FIG. 1, the system 10 includes multiple measurement sensors 26 and/or control sensors 28. Although only two of each of the measurement sensors 26 and control sensors 28 are illustrated, it should be understood that large numbers (e.g., tens or hundreds) of sensors 26, 28 may be deployed and monitored simultaneously. When multiple sensors 26, 28 are deployed, changes in the characteristic frequency of one or several of the measurement sensors 26 may be identified among the characteristic frequencies of the other sensors 26, 28. Applying multiple sensors 26, 28 increases the likelihood that sensors 26, 28 may fall on contaminated areas of the test object 50. Additionally, multiple sensors 26, 28 may be capable of detecting extremely low levels of pathogen in a sample because only a few sensors 26, 28 are required to bind to pathogen. Multiple sensors 26, 28 may allow for compensation of environmental effects. In particular, the use of both measurement sensors 26 and control sensors 28 may compensate for environmental changes, such as temperature, humidity, and non-specific binding. Additionally or alternatively, multiple sensors 26, 28 may allow the detection of different pathogens simultaneously. In that example, several pairs of measurement sensors 26 and control sensors 28 may be used, with each group of measurement sensors 26 including a biorecognition element 36 targeted to a different pathogen.

The system 10 may further include a magnetic field generator 30 configured to generate a constant, uniform magnetic field 32. The uniform magnetic field 32 extends through the test object 50, or through a part of the test object 50 that is under test. As described further below in connection with the method 100 of FIG. 5, the uniform magnetic field 32 may align the measurement sensors 26 and/or the control sensors 28. Alignment of the sensors 26, 28 may improve the sensitivity, signal-to-noise ratio, or other operating characteristics of the sensors 26, 28 and/or the test coil 20 and thereby improve accuracy of the system 10. The uniform magnetic field 32 may also bias the sensors 26, 28 during application of the varying magnetic field 24, increasing the magnitude of the response signal. The magnetic field generator 30 may be embodied as any component capable of generating the uniform magnetic field 32, for example, a pair of permanent magnet arrays or a Helmholtz coil.

Figure 2:
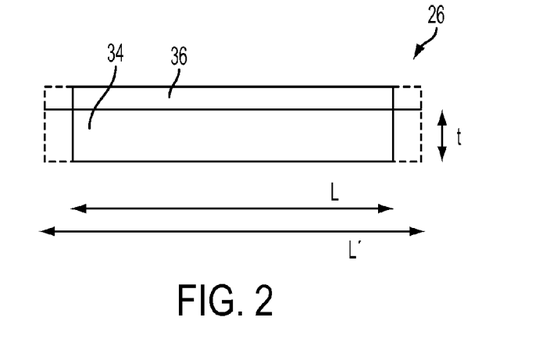
FIG. 2 is a simplified cross-sectional diagram of a magnetoelastic sensor of the system of FIG. 1.

Referring now to FIG. 2, a simplified schematic diagram of one illustrative embodiment of a measurement sensor 26 of the system 10 is shown. The sensor 26 includes a body 34 coated with an immobilized biorecognition element 36. The body 34 is made from a magnetoelastic material, such as a magnetostrictive alloy. In one illustrative embodiment, the body 34 may be mechanically polished and cut (diced) from a strip of METGLAS™ 2826 MB, which is commercially available from Honeywell Inc., of Conway, S.C.

In the illustrative embodiment, each measurement sensor 26 has a length L, a thickness t, and a width w (not shown). The measurement sensor 26 is in the shape of a thin strip, meaning that the length L is larger than the width w and much larger than the thickness t (i.e., L>w>>t). Upon application of the varying magnetic field 24, the dimensions of the measurement sensor 26 change. Accordingly, the measurement sensor 26 mechanically vibrates in response to the varying magnetic field 24. In particular, due to its thin strip shape, the measurement sensor 26 vibrates mainly longitudinally; in other words, when an oscillating external magnetic field is applied, the measurement sensor 26 vibrates between the length L and a length L'. The fundamental resonant frequency of this longitudinal oscillation is given as:

$$f_0 = \frac{V}{2L}, \quad (1)$$

where V is the acoustic velocity of the material along its length L. Addition of a small mass ($\Delta m<<M$) on the measurement sensor 26 surface causes a change in the resonant frequency ($\Delta f$). This resonant frequency change is proportional to the initial frequency $f_0$ and the mass added ($\Delta m$) and is inversely proportional to the initial sensor mass M. Assuming the added mass is uniformly distributed on the surface of the sensor 26, the resonant frequency change may be approximated as:

$$\Delta f = -\frac{f_0 \Delta m}{2M}(\Delta m << M). \quad (2)$$

The negative sign in Equation (2) means that the resonant frequency of the measurement sensor 26 decreases with the increase of the mass load. The additional mass load on the measurement sensor 26 can be obtained by measuring the shift in the resonant frequency (or another characteristic frequency related to the resonant frequency).

When the measurement sensor 26 comes into contact with the target pathogens, the biorecognition element 36 immobilized on the measurement sensor 26 surface will bind/capture the target pathogen. This adds an additional mass load on the measurement sensor 26. This additional mass causes a drop in a characteristic frequency of the measurement sensor 26. Therefore, the presence of any target pathogens can be identified by monitoring for a shift in the characteristic frequency of the measurement sensor 26. In some embodiments, a measurement sensor 26 with a length L less than 50 μm may have the capability of producing a frequency shift that represents the mass of single bacteria cell. It is contemplated that, in other embodiments, other configurations of the measurement sensor 26, such as a bar with the length of L and diameter of d, may also be used as the measurement sensor 26. For the measurement sensors 26 in bar shape, the length should be much larger than the diameter (L>>d).

The simple strip-shaped configuration of the illustrative measurement sensor 26 described above may make fabrication relatively easy and/or inexpensive. Additionally, the measurement sensors 26 are passive sensors that do not require on-board power or any wire physically connected to the other components of the system 10. As described above, the measurement sensor 26 may be fabricated by mechanical methods (e.g., polish and dice) or by microelectronics fabrication methods (e.g., sputter deposit, thermal deposit, or electrochemical deposit). These methods can mass-produce fabricated measurement sensors 26 with very low cost. For example, given measurement sensors 26 with the size of 2×10×50 μm, more than one million measurement sensors 26 may be fabricated from a single four-inch silicon wafer. In that example, the cost of fabrication of a single measurement sensor 26 may be less than 1/1000 of a cent. Additional details of illustrative magnetoelastic ligand detectors are described in U.S. Pat. No. 7,759,134 ("Magnetostrictive Ligand Sensor"), the entire disclosure of which is incorporated herein by reference.

As described above, the biorecognition element 36 may be immobilized on the surface of each measurement sensor 26 to bind a specific target pathogen. In some embodiments, the biorecognition element 36 may be embodied as a chemical binding element or an interaction layer immobilized on the body 34 of the measurement sensor 26. For example, the biorecognition element 36 may be a traditional antibody. Additionally or alternatively, in some embodiments, the biorecognition element 36 may be a genetically engineered bacteriophage ("phage"). The use of phages as a substitute for antibodies offers a stable, reproducible, and inexpensive alternative. In particular, phages have high affinity for binding with target pathogen cells, the phage structure is robust and stable, and phages may bind target pathogens in air with certain humidity. Specific ligand recognition devices that may be illustratively used as the biorecognition element 36, as well as illustrative application methods, are discussed in U.S. Pat. No. 7,138,238 ("Ligand Sensor Devices and Uses Thereof"), U.S. Pat. No. 7,267,993 ("Phage Ligand Sensor Devices and Uses Thereof"), and U.S. Pat. No. 7,670,765 ("Method of Forming Monolayers of Phage-Derived Products and Used Thereof"), the entire disclosures of which are incorporated herein by reference.

In one illustrative embodiment, the biorecognition element 36 may be a genetically engineered filamentous phage known as the E2 class of phage (including variants E2A, E2B, et al.). The illustrative E2 phage is configured to specifically bind with *Salmonella*, even in masked solutions containing very large concentrations of other bacteria. For example, in one embodiment the E2 phage may detect *Salmonella* in a solution masked by $10^7$ CFU/mL common *E. coli* or in a solution masked by $10^7$ CFU/mL common *E. coli* and $10^7$ CFU/mL *Listeria*. In other embodiments, the biorecognition element 36 may be other filamentous phages genetically engineered to have binding affinity under harsher environments or to bind specifically with different pathogens (e.g., different food-borne bacteria cells). In some embodiments, the biorecognition element 36 may be immobilized on the surface of the measurement sensor 26 using physical adsorption.

Figure 3:
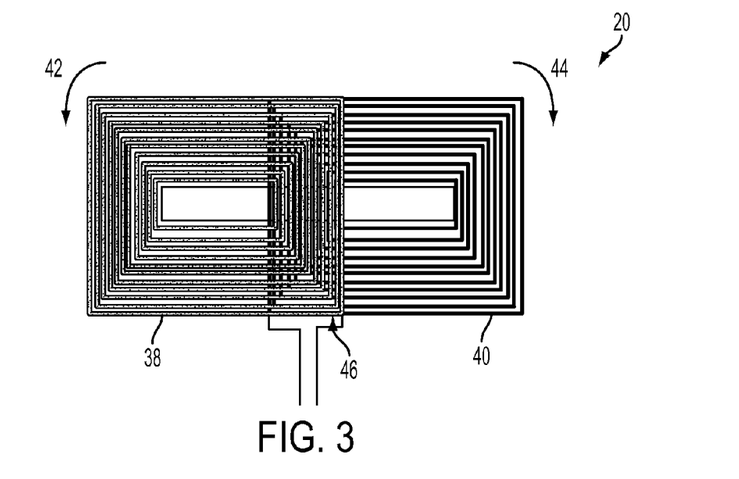
FIG. 3 is a simplified plan view of one illustrative embodiment of a test coil of the system of FIG. 1.
Figure 4:
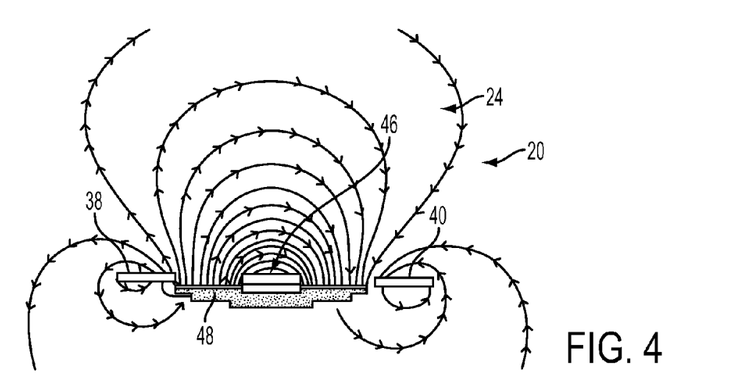
FIG. 4 is a simplified cross-sectional diagram of a magnetic field generated by the test coil of FIG. 3.

Referring now to FIGS. 3 and 4, one illustrative embodiment of the test coil 20 is shown. As described above, in some embodiments, the test coil 20 may be embodied as a focused-field flat coil. An illustrative focused-field flat coil 20 of the "Figure-8" or "butterfly" configuration, which includes a pair of rectangular coils 38, 40, is shown. Each of the rectangular coils 38, 40 may be embodied as a flat spiral inductor fabricated directly on a PCB. In the illustrative embodiment shown in FIG. 3, each of the turns (i.e., loops) of the coils 38, 40 has a rectangular shape. Of course, while the illustrative focused-field flat coil 20 includes a rectangular coil design, no specific geometrical pattern is required. Further, each of the rectangular coils 38, 40 has a winding direction 42, 44, respectively. The winding directions 42, 44 are opposite of each other. That is, if the winding direction 42 is counterclockwise then the winding direction 44 is clockwise, and vice versa. The rectangular coils 38, 40 are positioned such that they partially overlap. The overlapping portions of the coils 38, 40 define a sensing region 46. As shown in FIG. 4, the varying magnetic field 24 generated by the focused-field flat coil 20 extends outside of the inner volume 22 of the coil 20 and is strongest over the sensing region 46.

To increase the magnetic field strength generated by the test coil 20, in some embodiments the test coil 20 may include a backing 48 made of a high magnetic permeability material (best seen in FIG. 4). The high magnetic permeability material may comprise an amorphous metal alloy, permalloy, soft iron, and/or another suitable material. The backing 48 may be placed behind the sensing region 46 alone, or behind the inner diameters of the coils 38, 40. Positioning the backing 48 on one side of the focused-field flat coil 20 increases the magnetic field strength on the opposite side of the coil 20. For example, in some embodiments, without the backing 48 a 90 mG magnetic field contour line may extend 2.7 mm above the plane of the test coil 20. In some embodiments, with the backing 48 placed behind the sensing region 46, the 90 mG magnetic field contour line may extend 4.2 mm above the plane of the test coil 20. Further, in some embodiments, with the backing 48 approximately reaching the inner diameters of the coils 38, 40, the 90 mG magnetic field contour line may extend 4.8 mm above the plane of the test coil 20.

Figure 5:
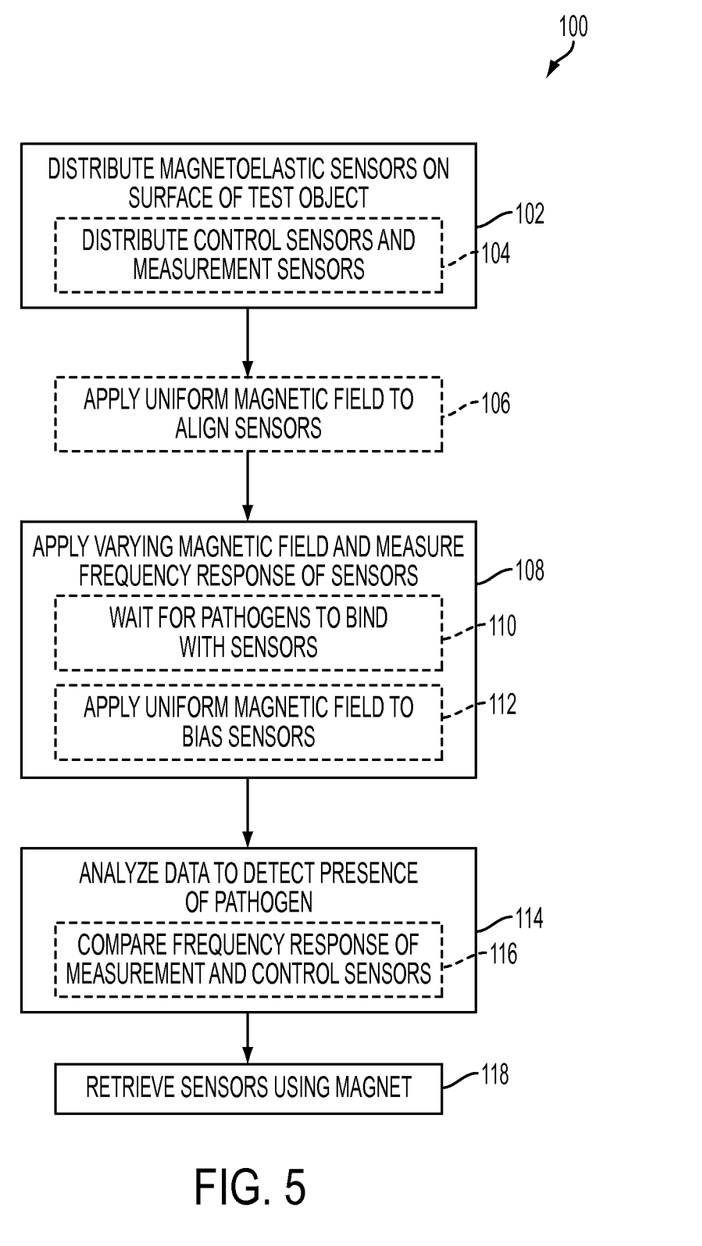
FIG. 5 is a simplified flow diagram of one embodiment of a method for in-situ pathogen detection that may be performed using the system of FIG. 1.

Referring now to FIG. 5, one illustrative embodiment of a method 100 that may be used by the in-situ pathogen detection system 10 is shown as a simplified flow diagram. The method 100 is illustrated as a series of blocks 102-118, some of which may be optionally performed in some embodiments (and, thus, are shown in dashed lines). It will be appreciated by those of skill in the art that some embodiments of the method 100 may include additional or different processes and sub-processes.

The method 100 begins with block 102, in which a number of measurement sensors 26 are distributed on a surface of the test object 50. In some embodiments, block 102 may also optionally include block 104, in which a number of control sensors 28 are distributed on the surface of the test object 50. As mentioned above, the frequency response of the control sensors 28 may be used to compensate for the effects of environmental changes, such as temperature, humidity, and non-specific binding, allowing increased detection accuracy. The distribution of the measurement sensors 26 (and, optionally, the control sensors 28) may be conducted manually or using a sensor distribution device. Distribution of the measurement sensors 26 (and, optionally, the control sensors 28) may be accomplished in a relatively short time (e.g., thirty seconds).

After block 102, the method 100 may, in some embodiments, optionally proceed to block 106, in which the uniform magnetic field 32 is applied to the measurement sensors 26 (and, where used, the control sensors 28). The uniform magnetic field 32 aligns the sensors 26, 28 in the direction of the uniform magnetic field 32. This alignment of the sensors 26, 28 causes the longitudinal oscillation of all (or, at least, most) of the sensors 26, 28 to be in the same direction. In this way, the test coil 20 may not need to align with individual sensors 26, 28. The magnetic flux picked up by the test coil 20 may thus contain frequency response information for all (or, at least, most) of the sensors 26, 28. Additionally or alternatively, the uniform magnetic field 32 may polarize the magnetoelastic material of the sensors 26, 28, resulting in amplified and quasi-linear response. In some embodiments, blocks 102 and 106 may be performed simultaneously. In other words, distributing the measurement sensors 26 and/or the control sensors 28 within the uniform magnetic field 32 may automatically align the sensors 26, 28 as the sensors 26, 28 fall on the surface of the test object 50.

As an alternative to block 106 (i.e., instead of using a magnetic field generator 30 to produce the uniform magnetic field 32), the method 100 may involve aligning the test coil 20 with individual sensors 26, 28. By way of example, a permanent magnet may be integrated with the test coil 20 to produce a constant magnetic field that is aligned with the varying magnetic field 24 generated by the test coil 20. In such an embodiment, when the test coil 20 is moved close to a sensor 26, 28 already distributed on the surface of the test object 50, the sensor 26, 28 may align locally with the integrated magnet's field. If the sensor 26, 28 does not align based on the integrated permanent magnet, the direction of the test coil 20 may be adjusted (manually or electronically controlled) until the sensor 26, 28 and the test coil 20 are aligned.

After block 106 (or after block 102, in embodiments not employing block 106), the method 100 proceeds to block 108. In block 108, the varying magnetic field 24 is applied to the sensors 26, 28 and the frequency response of the sensors 26, 28 is measured. As the sensors 26, 28 are distributed on the surface of the test object 50, the measurement sensors 26 may make contact with the target pathogen if the measurement sensors 26 fall on a contaminated area. As described above, the measurement sensors 26 include the biorecognition element 36 that will bind with target pathogens upon contact with the specific target pathogen. Binding with the pathogen increases the mass of the measurement sensor 26, which causes a characteristic frequency of the measurement sensor 26 to decrease. The decrease in characteristic frequency is proportional to the additional mass of bound bacteria. The initial characteristic frequencies of both the measurement sensors 26 and the control sensors 28, as well as the changes in their characteristic frequencies, may be monitored and recorded by the controller 12 using the test coil 20. In some embodiments, block 108 may involve waiting for any pathogens present to bind with the measurement sensors 26, as illustrated in block 110. For example, the measurement sensors 26 may be allowed to sit on the surface of the test object 50 for several minutes in order to allow binding to occur. Furthermore, in some embodiments, block 108 may also involve applying the uniform magnetic field 32 to the sensors 26, 28 (while the varying magnetic field 24 is applied), as illustrated in block 112. In such embodiments, the uniform magnetic field 32 may bias the sensors 26, 28 and increase the magnitude of the response signal.

The characteristic frequencies of the measurement sensors 26 and/or the control sensors 28 may be excited and detected by the test coil 20. For example, a current may be applied to the test coil 20 by the controller 12 to cause the test coil 20 to generate the varying magnetic field 24. The varying magnetic field 24 will then cause the magnetoelastic sensors 26, 28 to oscillate. As each sensor 26, 28 is mechanically oscillating, the sensor 26, 28 emits and/or causes small perturbations to the magnetic flux that may be detected through electromagnetic signals resulting from mutual inductive coupling with the test coil 20. At a particular frequency, there is an optimum transfer coupling of mechanical energy to magnetic energy. The controller 12 may compare the applied signal and the feedback signal to detect this characteristic frequency. In particular, the controller 12 may analyze a signal indicative of the impedance of the test coil 20, such as the input port voltage reflection coefficient (the $S_{11}$ parameter) of the test coil 20. The controller 12 may monitor the characteristic frequency in real time or record data for later analysis.

While applying the varying magnetic field 24, the test coil 20 may be moved to a position close to the measurement sensors 26 and/or the control sensors 28. The position should be close enough that the test coil 20 can excite the sensors 26, 28 and detect the corresponding oscillatory response signal from the sensors 26, 28. In some embodiments, the relative positions of the test coil 20 and the test object 50 may be adjusted manually or electronically using a positioning stage or table. However, throughout detection, the sensors 26, 28 remain positioned outside of the inner volume 22 of the test coil 20.

The frequency of the varying magnetic field 24 may be varied through a range of frequencies. The range of frequencies may include a characteristic frequency of the measurement sensors 26 and/or the control sensors 28 when the target pathogen has not been bound (i.e., the sensors 26, 28 are unloaded). In some embodiments, the range of frequencies to be applied by the test coil 20 may be determined using the following method. Assume the unloaded characteristic frequency for the measurement sensors 26 is A, while B is the unloaded characteristic frequency for the control sensors 28. As mentioned above, A and B may be slightly different to distinguish the response of the measurement sensors 26 from that of the control sensors 28. For example, A may be slightly smaller than B. In this example, the range of frequencies applied by the test coil 20 may cover from 50% of A to slightly more than B. Binding of target pathogens on the measurement sensor 26 surface is typically a small mass change and, the decrease in the characteristic frequency of the measurement sensors 26 due to this small mass change is normally less than 50% of the unloaded characteristic frequency of the measurement sensor 26. Decreases in characteristic frequency beyond that range are unlikely to be due to pathogen binding.

After applying the varying magnetic field 24 in block 108, the method 100 proceeds to block 114, in which the controller 12 analyzes collected data to determine whether the pathogen is present. During block 114, the controller 12 may determine whether the characteristic frequency of the measurement sensors 26 has shifted. The characteristic frequency shifting by a sufficient amount (and/or the characteristic frequency shifting for a sufficient number of measurement sensors 26) may indicate that the target pathogen is present.

In some embodiments, block 114 may involve comparing the measured frequency responses of the measurement sensors 26 and the control sensors 28, as illustrated in block 116. A statistically significant difference between the frequency responses of the measurement sensors 26 and the control sensors 28 may indicate the presence of the target pathogen. For example, frequency shifts measured for the measurement sensors 26 may have large variation for a given concentration of pathogen. However, there still may be a statistically significant difference between the frequency shifts of the measurement sensors 26 and the control sensors 28 for all pathogen concentrations of 500 CFU/ml and higher. In one illustrative embodiment, the measurement sensor 26 and control sensor 28 frequency shifts may be statistically evaluated using the Student's t-test. It will be appreciated that, in other embodiments, other statistical methods for evaluating the measured data may be used by the controller 12.

Figure 7:
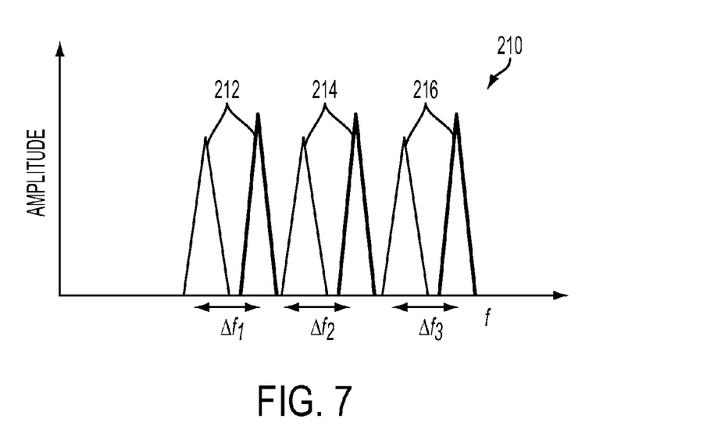
FIG. 7 is yet another exemplary plot of magnetoelastic sensor frequency response that may be measured using the system of FIG. 1.

Additionally, in some embodiments, the system 10 may monitor for different pathogens simultaneously using measurement sensors 26 including different biorecognition elements configured to bind with different pathogens. In such embodiments, measurement sensors 26 configured to detect different pathogens may have different unloaded characteristic frequencies, allowing the system 10 to distinguish the frequency response of each group of measurement sensors 26. For example, referring now to FIG. 7, an exemplary plot 210 illustrates frequency response curves that may be measured for three groups of measurement sensors 26 (each configured to detect a different pathogen). In the illustrative example, curve 212 illustrates a frequency response and frequency shift $\Delta f_1$ for measurement sensors 26 targeting one pathogen, curve 214 illustrates a frequency response and frequency shift $\Delta f_2$ for measurement sensors 26 targeting another pathogen, curve 216 illustrates a frequency response and frequency shift $\Delta f_3$ for measurement sensors 26 targeting yet another pathogen. Thus, in that example, the system 10 may simultaneously, independently test for multiple pathogens on the same test object 50.

In some embodiments, block 108 and block 114 may be performed simultaneously, such that pathogen detection may be conducted in real-time. In those embodiments, the characteristic frequencies of the measurement sensors 26 and the control sensors 28 may be monitored and recorded as a function of time. That data may be analyzed by the controller 12. If differentiation between the frequency shifts in the measurement sensors 26 and the control sensors 28 are observed, the presence of target pathogens may be confirmed and the system 10 may give a positive result for the pathogen detection test. If after a certain binding/detection time (such as 15 minutes) there is no statistical difference detected between the frequency shifts for the measurement sensors 26 and the control sensors 28, a negative result may be obtained for the pathogen detection test.

As described above, the system 10 may be used with large numbers of measurement sensors 26 and/or control sensors 28. Even when multiple sensors 26, 28 are used, the characteristic frequency shift of even one sensor 26 may be picked up out of many sensors 26, 28. In one illustrative example, ten measurement sensors 26 may be scanned together. When unloaded, the system 10 may observe a single large peak in the frequency response spectra because the sensors 26 all have the same unloaded characteristic frequency. Continuing that example, the ten sensors 26 may be scanned together again after applying a mass load to one sensor 26. The shift in characteristic frequency of the sensor 26 causes a single small peak in the frequency response spectra that can be easily identified.

Figure 6A:
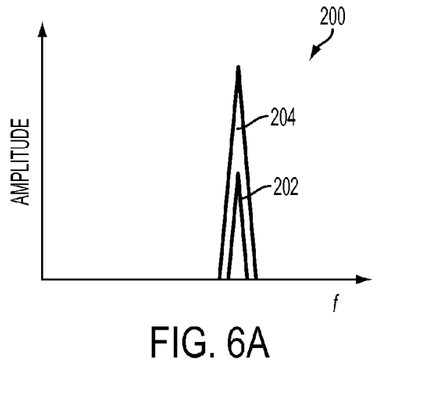
FIG. 6A is an exemplary plot of magnetoelastic sensor frequency response that may be measured using the system of FIG. 1.
Figure 6B:
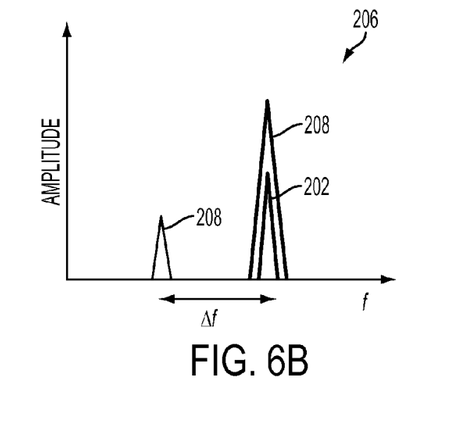
FIG. 6B is another exemplary plot of magnetoelastic sensor frequency response that may be measured using the system of FIG. 1.

Referring now to FIG. 6A, an exemplary plot 200 illustrates results that may be measured for a negative test, that is, when the pathogen is not detected. Plot 200 illustrates signal amplitude against frequency f. Curve 202 illustrates the frequency response for the control sensors 28, including a single peak at the unloaded characteristic frequency. Curve 204 illustrates the frequency response for the measurement sensors 26, including a single peak at the unloaded characteristic frequency. The characteristic frequencies of the measurement sensors 26 and the control sensors 28 are the same, representing that the pathogen has not been detected. Referring to FIG. 6B, an exemplary plot 206 illustrates results that may be achieved for a positive test, that is, when the pathogen is detected. Curve 202 again illustrates the frequency response for the control sensors 28. Curve 208 illustrates the frequency response of the measurement sensors 26 and includes a strong peak at the unloaded characteristic frequency and a smaller peak shifted to a lower frequency by amount $\Delta f$. These results may indicate that some of the measurement sensors 26 have bound with the pathogen and experienced a frequency shift.

After analyzing the data in block 114, the method 100 may advance to block 118, in which the measurement sensors 26 and/or the control sensors 28 are retrieved from the surface of the test object 50 using a magnet. For example, block 118 may involve passing a permanent magnet or an electromagnet over the surface of the test object 50 to cause the measurement sensors 26 and/or the control sensors 28 to cling to the permanent magnet or the electromagnet. In some embodiments, the test object 50 may be disposed after retrieving the sensors 26, 28.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the apparatus, systems, and methods described herein. It will be noted that alternative embodiments of the apparatus, systems, and methods of the present disclosure may not include all of the features described yet still benefit from at least some of the advantages of such features. Those of ordinary skill in the art may readily devise their own implementations of the apparatus, systems, and methods that incorporate one or more of the features of the present disclosure.

The invention claimed is:

1. An in-situ pathogen detection system comprising:
    one or more magnetoelastic measurement sensors each including a biorecognition element configured to bind with a pathogen to cause a shift in a characteristic frequency of the associated measurement sensor;
    a test coil configured to (i) apply a uniform magnetic field to the one or more magnetoelastic measurement sensors, (ii) apply a varying magnetic field to the one or more magnetoelastic measurement sensors during application of the uniform magnetic field, and (iii) detect a frequency response of the one or more magnetoelastic measurement sensors to the applied varying magnetic field, while the one or more magnetoelastic measurement sensors are positioned on a surface of a test object that is outside of an inner volume defined by the test coil; and
    a controller coupled to the test coil and configured to (i) transmit a first signal that causes the test coil to generate at least the varying magnetic field, (ii) receive a second signal indicative of the frequency response of the one or more magnetoelastic measurement sensors detected by the test coil, and (iii) determine whether the pathogen is present based on the second signal.

2. The in-situ pathogen detection system of claim 1, wherein the test coil is a focused-field flat coil.

3. The in-situ pathogen detection system of claim 1, wherein the test coil is further configured to apply the uniform magnetic field to align the one or more magnetoelastic measurement sensors prior to application of the varying magnetic field.

4. The in-situ pathogen detection system of claim 1, further comprising one or more magnetoelastic control sensors that do not include the biorecognition element;
    wherein the test coil is further configured to (i) apply the varying magnetic field to the one or more magnetoelastic control sensors and (ii) detect a frequency response of the one or more magnetoelastic control sensors to the applied varying magnetic field, while the one or more magnetoelastic control sensors are positioned on the surface of the test object; and
    wherein the second signal is also indicative of the frequency response of the one or more magnetoelastic control sensors detected by the test coil.

5. The in-situ pathogen detection system of claim 4, wherein the second signal is indicative of (i) a shifted characteristic frequency of the one or more magnetoelastic measurement sensors caused by binding of the biorecognition element with the pathogen and (ii) a control characteristic frequency of the one or more magnetoelastic control sensors.

6. The in-situ pathogen detection system of claim 5, wherein the controller is configured to determine whether the pathogen is present by determining whether the shifted characteristic frequency is statistically significantly less than the control characteristic frequency.

7. The in-situ pathogen detection system of claim 1, further comprising:
    one or more additional magnetoelastic measurement sensors each including a different biorecognition element configured to bind with a different pathogen to cause a shift in a characteristic frequency of the associated additional measurement sensor;
    wherein the test coil is further configured to (i) apply the varying magnetic field to the one or more additional magnetoelastic measurement sensors and (ii) detect a frequency response of the one or more additional magnetoelastic measurement sensors to the applied varying magnetic field, while the one or more additional magnetoelastic measurement sensors are positioned on the surface of the test object;
    wherein the second signal is also indicative of the frequency response of the one or more additional magnetoelastic measurement sensors detected by the test coil; and wherein the controller is further configured to determine whether the different pathogen is present based on the second signal.

8. The in-situ pathogen detection system of claim 1, wherein the test coil comprises a number of loops surrounding the inner volume and a glass core positioned within the inner volume.

9. The in-situ pathogen detection system of claim 8, wherein the test coil comprises a pair of partially overlapping flat coils having opposite winding directions.

10. The in-situ pathogen detection system of claim 9, wherein the test coil comprises a first side and a second side, and wherein the one or more magnetoelastic measurement sensors are positioned adjacent to the first side of the test coil and a backing formed of a high magnetic permeability material is coupled to the second side of the test coil.

11. The in-situ pathogen detection system of claim 1, wherein the test coil is configured to detect the frequency response by measuring a magnetic field generated by vibration of the one or more magnetoelastic measurement sensors in response to the applied varying magnetic field.

12. The in-situ pathogen detection system of claim 1, wherein the biorecognition element comprises a bacteriophage that is genetically engineered to bind with the pathogen.

13. The in-situ pathogen detection system of claim 1, wherein the first signal causes a frequency of the varying magnetic field generated by the test coil to vary through a range including the characteristic frequency of each of the one or more magnetoelastic measurement sensors when the biorecognition element has not bound with the pathogen.

14. The in-situ pathogen detection system of claim 13, wherein the range includes one or more values that are one half of the characteristic frequency of each of the one or more magnetoelastic measurement sensors when the biorecognition element has not bound with the pathogen.

15. The in-situ pathogen detection system of claim 13, wherein the second signal is indicative of an impedance of the test coil while varying the frequency of the varying magnetic field through the range.

16. The in-situ pathogen detection system of claim 1, wherein the uniform magnetic field applied by the test coil is aligned with the varying magnetic field applied by the test coil.

17. The in-situ pathogen detection system of claim 1, wherein the test coil comprises a permanent magnet configured to produce the uniform magnetic field.

18. The in-situ pathogen detection system of claim 1, wherein the first signal further causes the test coil to generate the uniform magnetic field.

* * * * *